(12) United States Patent
Bachmann et al.

(10) Patent No.: US 10,300,480 B2
(45) Date of Patent: May 28, 2019

(54) PIPETTING DEVICE FOR AN APPARATUS FOR PROCESSING A SAMPLE OR REAGENT, APPARATUS FOR PROCESSING A SAMPLE OR REAGENT AND METHOD FOR PIPETTING A SAMPLE OR REAGENT

(71) Applicant: Roche Molecular Systems, Inc., Pleasanton, CA (US)

(72) Inventors: Hans-Rudolf Bachmann, Buettikon (CH); Rolf Schneebeli, Mettmenstetten (CH)

(73) Assignee: Roche Molecular Systems, Inc., Pleasanton, CA (US)

( * ) Notice: Subject to any disclaimer, the term of this patent is extended or adjusted under 35 U.S.C. 154(b) by 0 days.

(21) Appl. No.: 15/291,960

(22) Filed: Oct. 12, 2016

(65) Prior Publication Data
US 2017/0131314 A1    May 11, 2017

(30) Foreign Application Priority Data
Oct. 13, 2015   (EP) .................................. 151895933

(51) Int. Cl.
*B01L 3/02*        (2006.01)
*G01N 35/10*       (2006.01)

(52) U.S. Cl.
CPC .......... *B01L 3/0279* (2013.01); *B01L 3/0227* (2013.01); *G01N 35/1009* (2013.01);
(Continued)

(58) Field of Classification Search
CPC ......... B01L 2200/16; B01L 2400/0487; B01L 3/0227; G01N 2035/1025;
(Continued)

(56) References Cited

U.S. PATENT DOCUMENTS 5,164,318 A * 11/1992 Sato ................. G01N 33/54306
                                                 422/504
8,119,080 B2   2/2012 Wiggli et al.
(Continued)

FOREIGN PATENT DOCUMENTS

EP    0189900 B1    4/1989
EP    2410342 A3    2/2012

OTHER PUBLICATIONS

Extended European Search Report for EP15189533.

*Primary Examiner* — Dennis White
*Assistant Examiner* — Bryan Kilpatrick
(74) *Attorney, Agent, or Firm* — Eric Grant Lee; Pamela Ancona

(57) ABSTRACT

A pipetting device (100) for an apparatus (164) for processing a sample or reagent is disclosed. The pipetting device (100) comprises a coupling mechanism (102), wherein the coupling mechanism (102) comprises at least a first coupling unit (104) adapted to be coupled to a first pipetting tip and a second coupling unit (106) adapted to be coupled to a second pipetting tip, and a tilt mechanism (112) for moving the first coupling unit (104) between an untilted position, in which the first coupling unit (104) and the second coupling unit (106) are arranged parallel to one another, and a tilted position, in which the first coupling unit (104) is tilted relative to the second coupling unit (106).

13 Claims, 12 Drawing Sheets

(52) U.S. Cl.
CPC ..... *G01N 35/1065* (2013.01); *G01N 35/1072* (2013.01); *G01N 35/1074* (2013.01); *G01N 35/1083* (2013.01); *B01L 2200/16* (2013.01); *B01L 2400/0487* (2013.01); *G01N 2035/103* (2013.01); *G01N 2035/1025* (2013.01); *G01N 2035/1086* (2013.01)

(58) Field of Classification Search
CPC ....... G01N 2035/1086; G01N 35/1009; G01N 35/1074; G01N 35/1083
See application file for complete search history.

(56) References Cited

U.S. PATENT DOCUMENTS

| | | | |
|---|---|---|---|
| 2001/0036425 A1* | 11/2001 | Gazeau | G01N 35/1067 422/400 |
| 2001/0039843 A1* | 11/2001 | Schoeppe | B01L 3/0279 73/863.32 |
| 2007/0178016 A1 | 8/2007 | Jost | |
| 2007/0264725 A1 | 11/2007 | Wiggli | |
| 2012/0186367 A1* | 7/2012 | D'Amore | G01N 35/1067 73/864.11 |

* cited by examiner

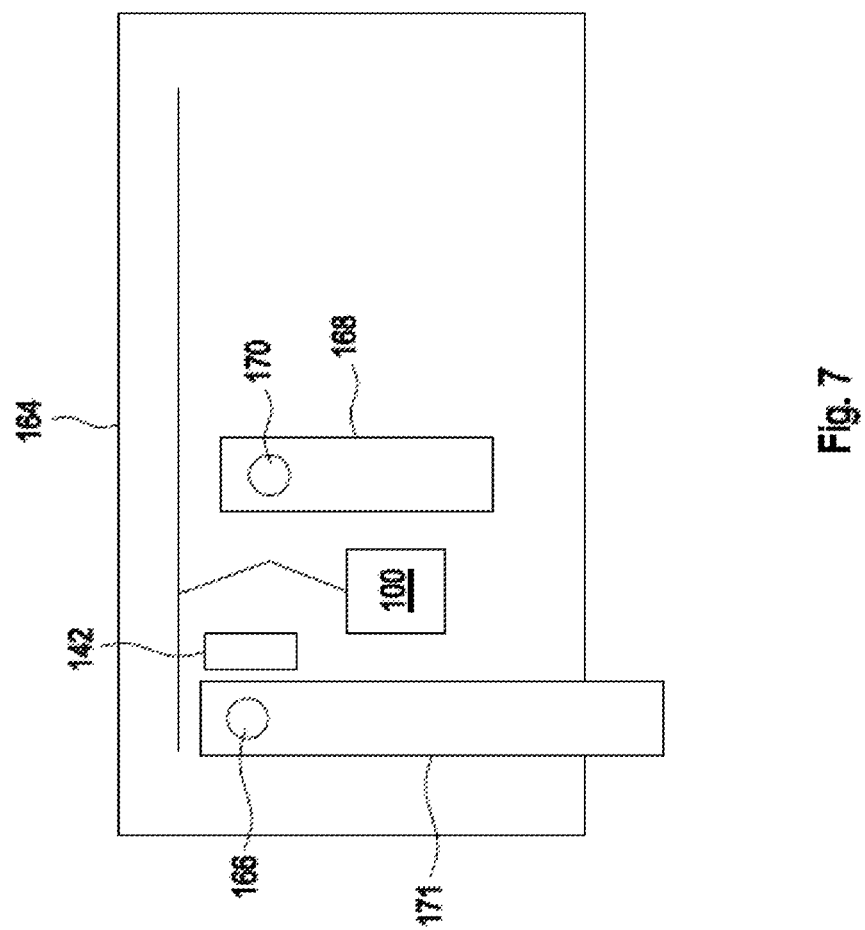

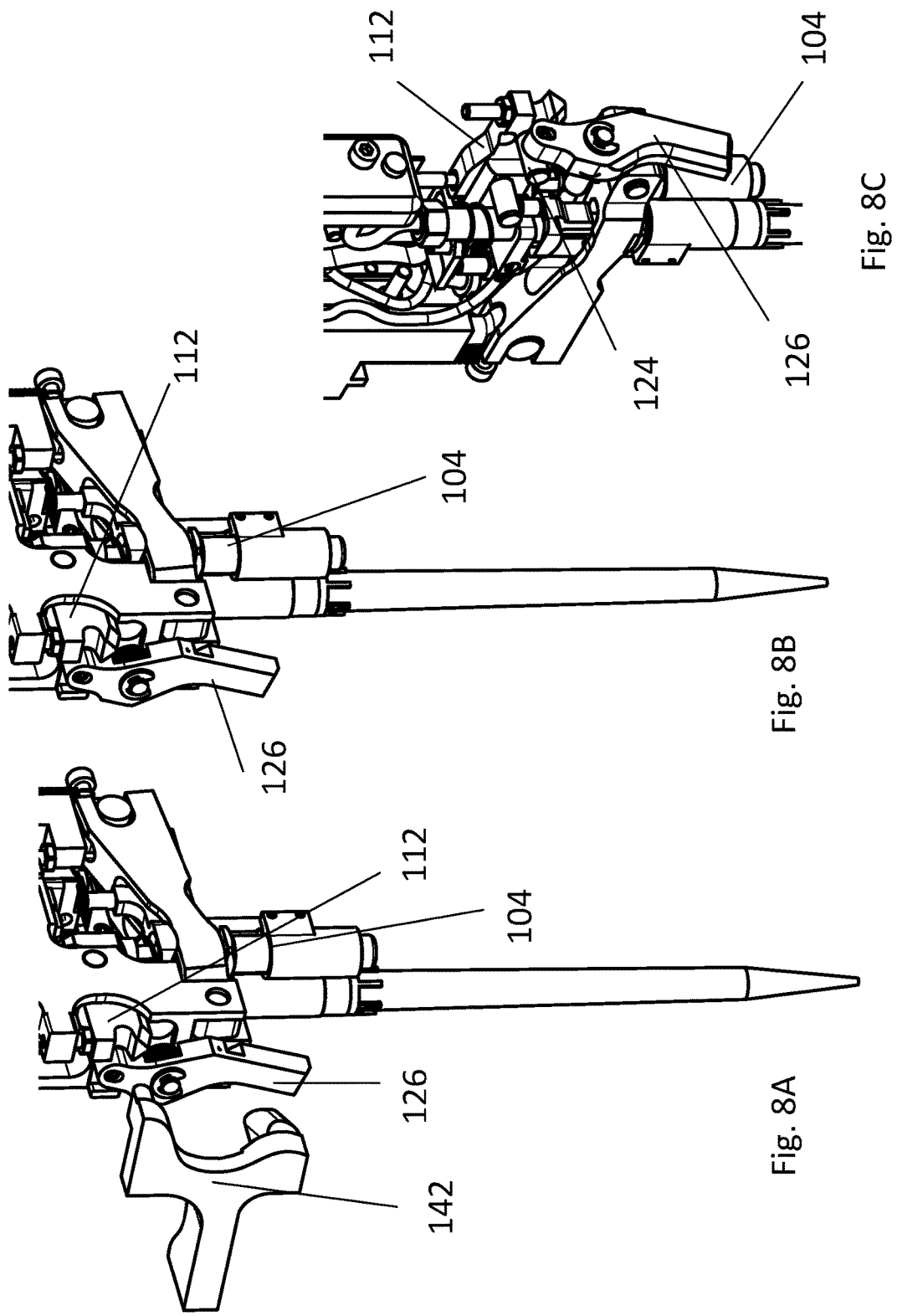

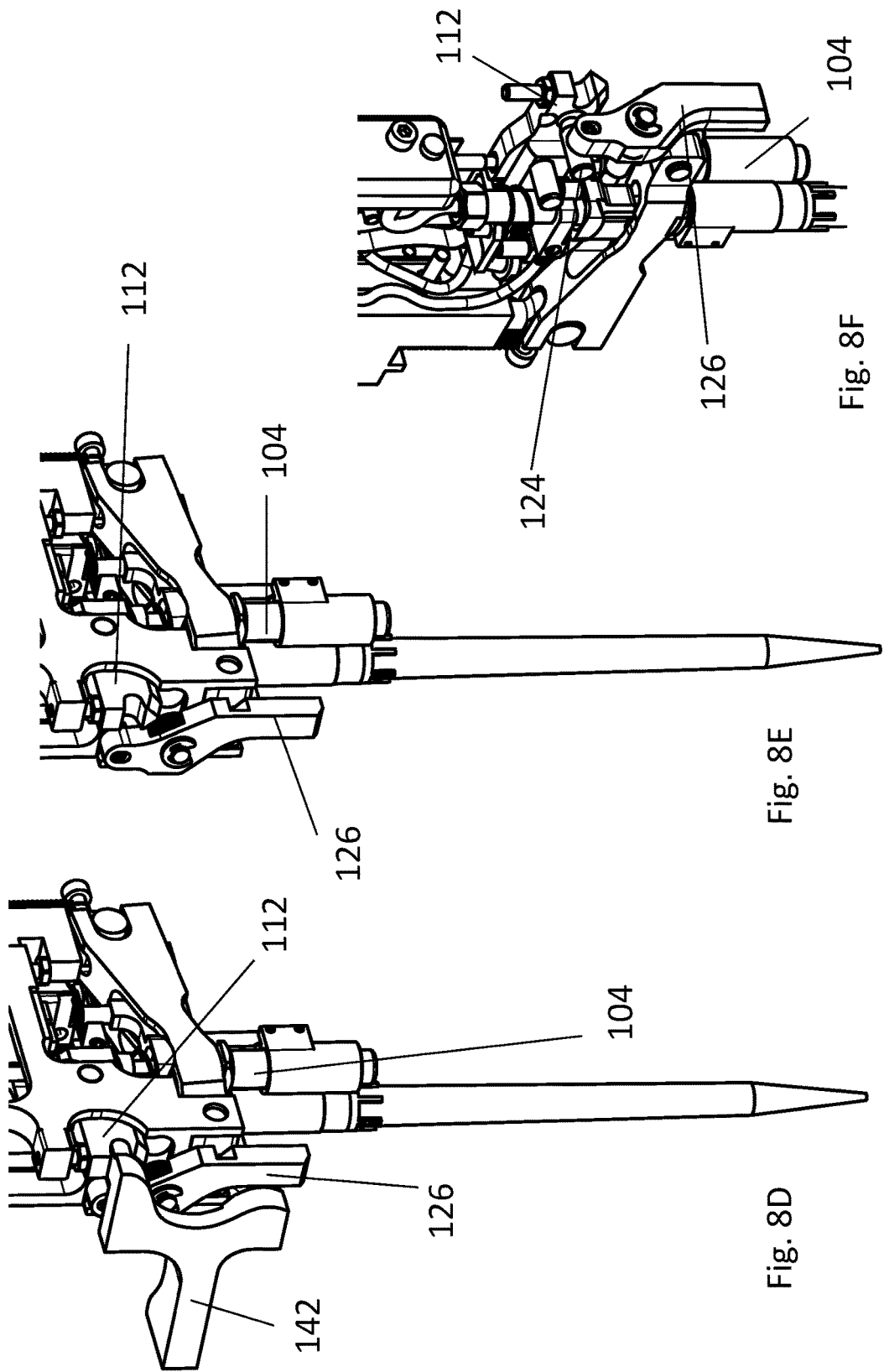

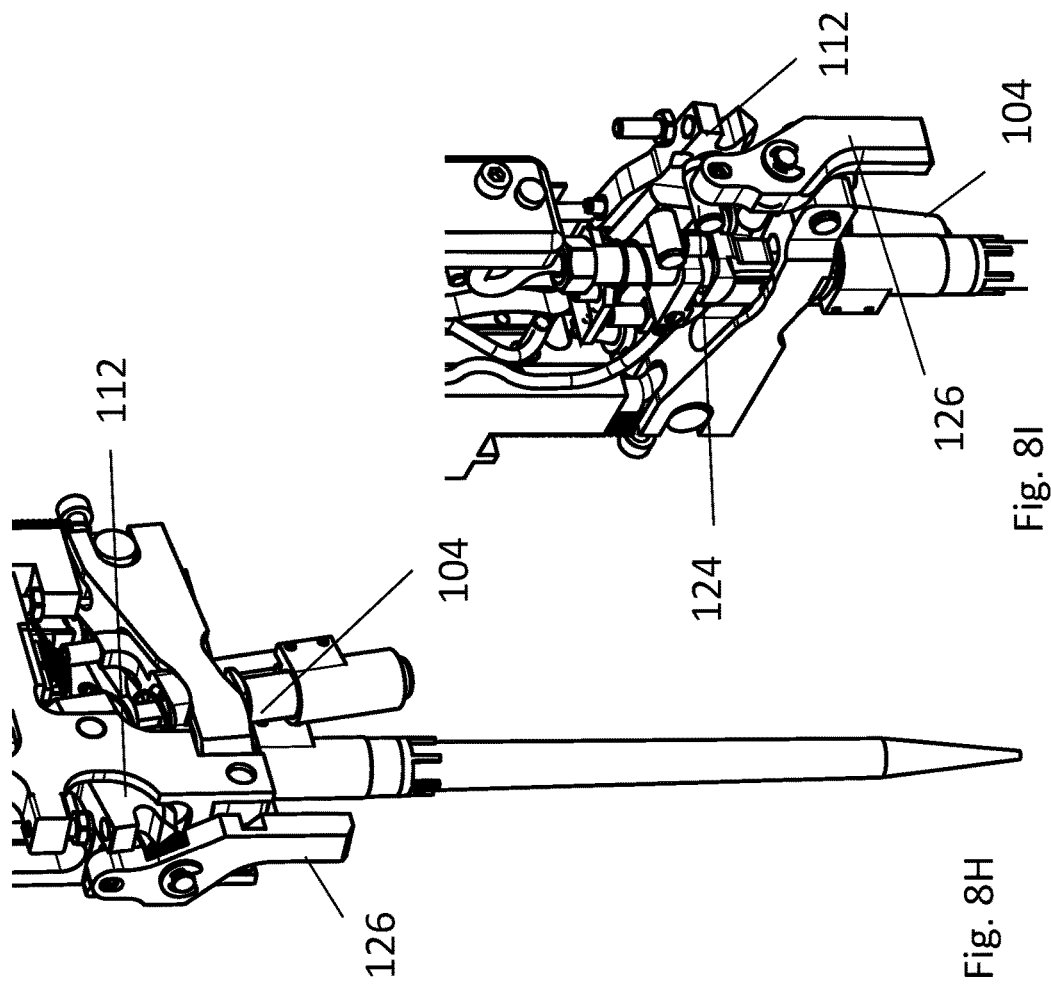
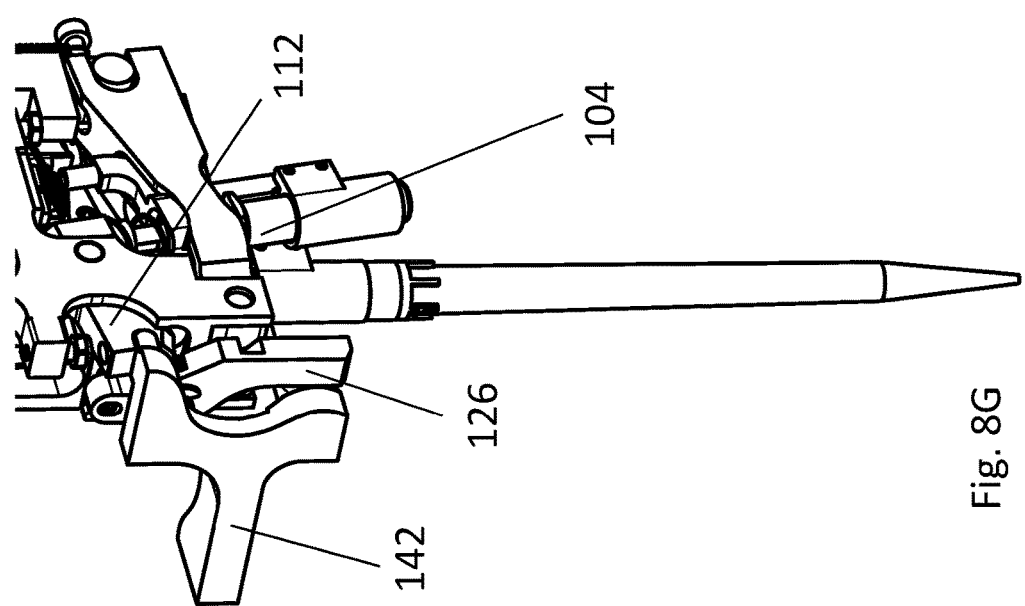

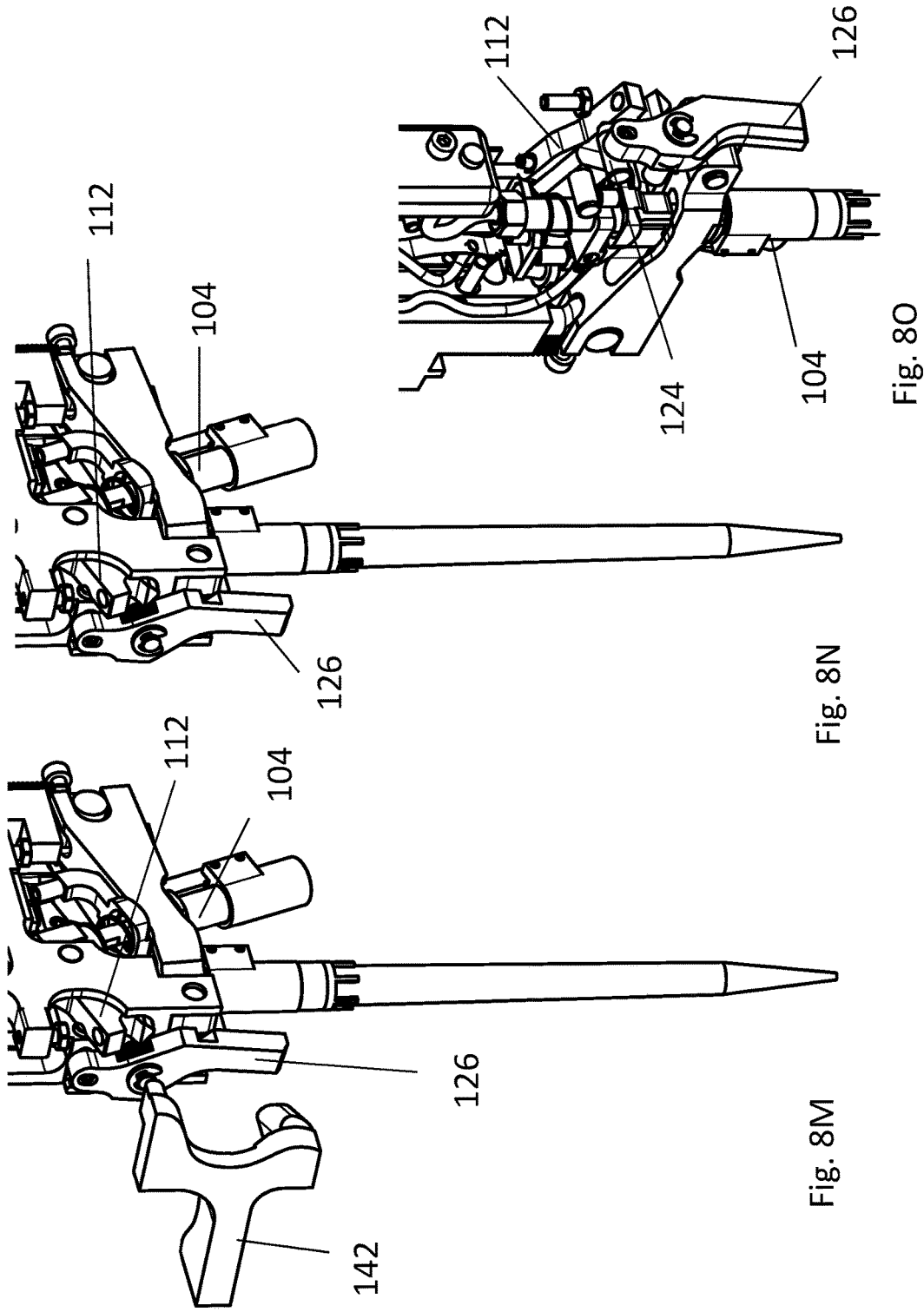

PIPETTING DEVICE FOR AN APPARATUS FOR PROCESSING A SAMPLE OR REAGENT, APPARATUS FOR PROCESSING A SAMPLE OR REAGENT AND METHOD FOR PIPETTING A SAMPLE OR REAGENT

CROSS-REFERENCE TO RELATED APPLICATIONS

This application claims the benefit of priority of EP Application No. 151895933, filed Oct. 13, 2015, the disclosure of which is incorporated herein by reference in its entirety. Reference is also made to EP Application No. 15189536.4, filed Oct. 13, 2015 (U.S. patent application Ser. No. 15/291,976, filed Oct. 12, 2016), the disclosure of which is also incorporated herein by reference in its entirety.

FIELD OF THE INVENTION

The present invention relates to a pipetting device for an apparatus for processing a sample or reagent, an apparatus for processing a sample or reagent, and a method for pipetting a sample or reagent.

BACKGROUND OF THE INVENTION

An apparatus for processing a sample or reagent in the sense of the present invention comprises a pipetting device. Such pipetting devices are used tor transferring a sample or reagent from a first vessel to a second vessel by means of an aspirating and dispensing operation. Modern apparatus for processing samples of this kind are largely fully automatic in operation and only the samples stored in the vessels have to be inserted into the apparatus and the desired process such as an analysis has to be entered.

The apparatus comprises at least an input for a first vessel comprising a sample or reagent. The apparatus further comprises a holder for holding a second vessel to which the sample or reagent from the first vessel is transferred by the pipetting device. Usually, the apparatus may comprise a plurality of first vessels and second vessels.

Using the above-described apparatus for processing a sample or reagent with pipetting devices having two pipetting tips provides advantages concerning the handling. Nevertheless, there are still some drawbacks. Particularly, there is a desire to minimize the clearance volume within the sample or a reagent such that the immersion depth is intended to be extended. The first vessels and the second vessels are arranged in a predetermined pattern. For example, with typical apparatus for processing samples, the distance between the vessels is 18 mm. The pipetting device comprises two pipetting tips. The first pipetting tip and the second pipetting tip are arranged at a distance of 9 mm. If one of the pipetting tips is used to aspirate a sample or a reagent from one of the vessels, the other pipetting tip abuts the upper end of this vessel at a predetermined immersion depth of for example 80-90 mm. Thus, the immersion depth of the pipetting, tips is limited due to the construction of the pipetting device.

It is therefore an objective of the present disclosure to provide a pipetting device, an apparatus for processing a sample or reagent and a method for pipetting a sample or a reagent which allows for an increased immersion depth, particularly of at least 100 mm, while preventing an abutment at the upper end of the vessel.

SUMMARY OF THE INVENTION

This problem is solved by a pipetting device, an apparatus for processing a sample or reagent and a method for pipetting a sample or a reagent with the features of the independent claims.

Thus, the specification provides a pipetting device for an apparatus for processing a sample or reagent, comprising a coupling mechanism, wherein the coupling mechanism comprises at least a first coupling unit adapted to be coupled to a first pipetting tip and a second coupling unit adapted to be coupled to a second pipetting tip, and a tilt mechanism for moving the first coupling unit between an untilted position, in which the first coupling unit and the second coupling unit are arranged parallel to one another, and a tilted position, in which the first coupling unit is tilted relative to the second coupling unit.

Also provided is an apparatus for processing a sample or reagent comprising a pipetting device as described herein, an input for a first vessel, said vessel comprising a sample or reagent, and a holder for holding a second vessel to which the sample or reagent is transferrable by the pipetting device.

Moreover, the specification provides a method for pipetting a sample or reagent using a pipetting device as described herein, comprising (a) coupling a second pipetting tip to the second coupling unit, (b) moving the first coupling unit from the untilted position, in which the first coupling unit and the second coupling unit are arranged parallel to one another, into the tilted position, in which the first coupling unit is tilted relative to the second coupling unit, and (c) aspirating a sample or reagent from a first vessel by means of the second pipetting tip while the first coupling unit is in the tilted position.

Still further, the specification includes a pipetting device for an apparatus for processing a sample or reagent, comprising a frame including the following elements arranged within and supported by the frame:

a coupling mechanism including at least a first coupling unit adapted to be coupled to a first pipetting tip and a second coupling unit adapted to be coupled to a second pipetting tip, a tilt mechanism configured to move the first coupling unit between an untilted position, in which the first coupling unit and the second coupling unit are arranged parallel to one another, and a tilted position, in which the first coupling unit is tilted relative to the second coupling unit, and a tilt mechanism trigger adapted to trigger the tilt mechanism by engagement with an activation device, wherein movement of the pipetting, device relative to the activation device engages with and activates the tilt mechanism, fixing the tilt mechanism in the untilted position, and thereby fixing the first coupling unit in the untilted position.

Therefore, the present disclosure provide a first embodiment of a pipetting device for an apparatus for processing a sample or reagent, comprising a coupling mechanism, wherein the coupling mechanism comprises at least a first coupling unit adapted to be coupled to a first pipetting tip and a second coupling unit adapted to be coupled to a second pipetting tip, and a tilt mechanism for moving the first coupling unit between an untilted position, in which the first coupling unit and the second coupling unit are arranged parallel to one another, and a tilted position, in which the first coupling unit is tilted relative to the second coupling unit. In this embodiment, the tilt mechanism can be tiltable around a first pivot.

Moreover, in the first embodiment, the pipetting device includes a tilt mechanism trigger adapted to trigger the tilt mechanism. The tilt mechanism trigger can be adapted to releasably fix the tilt mechanism in the untilted position. The tilt mechanism can include a first recess and the tilt mechanism trigger comprises a pin, wherein the tilt mechanism is fixable in the untilted position by means of an engagement of the pin with the first recess. Still further, the tilt mechanism trigger has a trigger lever adapted to pivot around a second pivot and optionally, the pin is connected to the trigger lever. Moreover, the tilt mechanism is releasable from the untilted position by means of a disengagement of the pin from the first recess. For example, the pin is selectively engageable with and disengageable from the first recess by means of pivoting the trigger lever around the second pivot. Thus, the tilt mechanism can be releasably fixable in the tilted position.

The first embodiment further provides a pipetting device wherein the coupling mechanism further comprises a first coupling lever connected to the first coupling unit, a second coupling lever connected to the second coupling unit, and a first coupling unit protrusion disposed on the first coupling unit, wherein the first coupling lever comprises a first coupling lever recess, wherein the tilt mechanism is releasably fixable in the tilted position by means of engagement of the first coupling unit protrusion with the first coupling lever recess. Therefore, the tilt mechanism is releasable from the tilted position by means of disengagement of the first coupling unit protrusion from the first coupling lever recess. The first coupling unit protrusion can be selectively engageable with and disengageable from the first coupling lever recess by means of pivoting the tilt mechanism around the first pivot. The tilt mechanism trigger can be adapted to be activated by means of engagement with an activation device of the apparatus for processing a sample and the tilt mechanism trigger can be adapted to be activated by means of a movement of the pipetting device relative to the activation device in a first direction.

In the first embodiment, the tilt mechanism comprises a second recess engageable with a protrusion of the activation device, wherein the tilt mechanism is tiltable around the first pivot by means of a movement of the pipetting device relative to the activation device in a second direction with the second recess engaged with the protrusion of the activation device. In this embodiment, the second direction is different from the first direction, e.g., the second direction is perpendicular to the first direction. The tilt mechanism can be tiltable around the first pivot by means of an actuator.

Moreover, the pipetting device of the first embodiment can include a sensor for detection whether the first coupling unit is in the untilted position or the tilted position, e.g., a Hall sensor. In addition, the pipetting device can include a magnet arranged at the tilt mechanism.

In another embodiment, the disclosure provides an apparatus for processing a sample or reagent comprising a pipetting device according to the first embodiment, an input for a first vessel, said vessel comprising a sample or reagent, and a holder for holding a second vessel to which the sample or reagent is transferrable by the pipetting device. The apparatus can include an activation device adapted to activate the tilt mechanism of the pipetting device. Moreover, the pipetting device of the apparatus can comprise a tilt mechanism trigger adapted to releasably fix the tilt mechanism in the untilted position, wherein the tilt mechanism trigger is adapted to be activated by means of engagement with the activation device. In this embodiment, the tilt mechanism trigger is adapted to be activated by means of a movement of the pipetting device relative to the activation device in a first direction. In a specific example, the tilt mechanism is tiltable around a first pivot by means of a movement of the pipetting device relative to the activation device in a second direction with the second recess engaged with the protrusion of the activation device. The second direction can be different from the first direction, e.g., the second direction is perpendicular to the first direction. The activation device can be arranged at the first vessel or the activation device is arranged spaced apart from the first vessel.

A third embodiment of the disclosure is a method for pipetting a sample or reagent using a pipetting device as described herein, the method including the following steps:
  coupling a second pipetting tip to the second coupling unit,
  moving the first coupling unit from the untilted position, in which the first coupling unit and the second coupling unit are arranged parallel to one another, into the tilted position, in which the first coupling unit is tilted relative to the second coupling unit, and
  aspirating a sample or reagent from a first vessel by means of the second pipetting tip while the first coupling unit is in the tilted position.

In the third embodiment, the first coupling unit can be moved into the tilted position if a ratio of a length of the second pipetting tip and a target immersion depth of the second pipetting tip into the first vessel is below a predetermined threshold. The tilt mechanism of the pipetting device can be activated by means of an activation device. The method can also include the step of transferring the sample or reagent to a second vessel by means of the pipetting device.

BRIEF DESCRIPTION OF THE FIGURES

Further features and embodiments of the invention will be disclosed in more detail in the subsequent description embodiments, preferably in conjunction with the dependent claims. Therein, the respective features may be realized in an isolated fashion as well as in any arbitrary feasible combination, as a skilled person will realize. The embodiments are schematically depicted in the figures. Therein, identical reference numbers in these figures refer to identical elements or functionally identical elements.

FIG. 7 shown a schematic illustration of an apparatus for processing as sample.

DETAILED DESCRIPTION OF THE INVENTION

Figure 1:
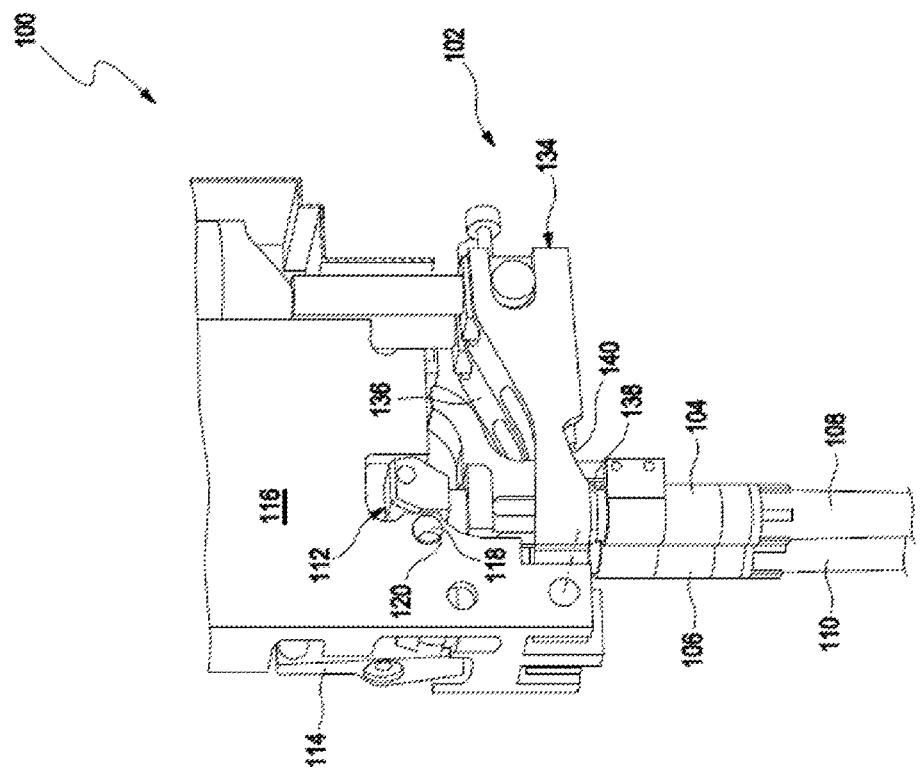
FIG. 1 shows a left side perspective view of a pipetting device as described herein.

According to the present invention, a pipetting device for an apparatus for processing a sample or reagent is disclosed. The pipetting device comprises a coupling mechanism, wherein the coupling mechanism comprises at least a first coupling unit adapted to be coupled to a first pipetting tip and a second coupling unit adapted to be coupled to a second pipetting tip, and a tilt mechanism for moving the first coupling unit between an untilted position, in which the first coupling unit and the second coupling unit are arranged parallel to one another, and a tilted position, in which the first coupling unit is tilted relative to the second coupling unit. Thus, according to the pipetting device of the present invention, the first coupling unit may be moved away from the second coupling unit by means of the pivotal movement. Thereby, a pipetting tip coupled to the second coupling unit may be immersed deeper into a vessel as the first coupling unit does not obstruct an immersion movement of the second coupling unit if tilted relative to the second coupling unit.

The term "sample", as used herein, refers to a material suspected of containing an analyte of interest. The sample can be derived from any biological source, such as a physiological fluid, including, blood, saliva, ocular lens fluid, cerebral spinal fluid, sweat, urine, milk, ascites fluid, mucous, synovial fluid, peritoneal fluid, amniotic fluid, tissue, cells or the like. The test sample can be pretreated prior to use, such as preparing plasma from blood, diluting viscous fluids, lysis or the like; methods of treatment can involve filtration, distillation, concentration, inactivation of interfering components, and the addition of reagents. A sample may be used directly as obtained from the source or following a pretreatment to modify the character of the sample, e.g. after being diluted with another solution or after having being mixed with reagents e.g. to carry out one or more diagnostic assays like e.g. clinical chemistry assays, immunoassays, coagulation assays, nucleic acid testing, etc. The term "sample" as used herein is therefore not only used for the original sample but also relates to a sample which has already been processed (pipetted, diluted, mixed with reagents, enriched, having been purified, having been amplified etc.). As used herein, the term "analyte" refers to the compound or composition to be detected or measured.

The term "reagent" is used to indicate a composition required for treatment of a sample. Reagents may be any liquid, e.g. a solvent or chemical solution, which needs to be mixed with a sample and/or other reagent in order e.g. for a reaction to occur, or to enable detection. A reagent may be for example a diluting liquid, including water, it may comprise an organic solvent, it may comprise a detergent, it may be a buffer. Reagents may also be dry reagents adapted e.g. to be dissolved by a sample, another reagent or a diluting liquid. A reagent in the more strict sense of the term may be a liquid solution containing a reactant, typically a compound or agent capable e.g. of binding to or chemically transforming one or more analytes present in a sample. Examples of reactants are enzymes, enzyme substrates, conjugated dyes, protein-binding molecules, nucleic acid binding molecules, antibodies, chelating agents, promoters, inhibitors, epitopes, antigens, etc.

The term "processing a sample" may relate to transferring, aliquoting, isolating, purifying, incubating, treating or reacting a sample or combining a reagent with a sample.

It is to be noted that the terms "first" and "second" are exclusively used with the present invention to conceptually distinguish between the respective constructional members and are not intended to indicate any order of importance or the like.

The term "pipetting tip" as used with the present invention covers disposable pipetting tips, which may be used only with a single pipetting process, and reusable pipetting tips, which may be used with more than one pipetting process. Disposable pipetting tips are usually made of plastics and are disposed after the pipetting process. Reusable pipetting tips may be designed as pipetting needles and are usually made of metal or any other material suitable for use with the respective samples. Accordingly, the term "coupled to" as used with the present invention in connection with the coupling of a pipetting tip to a coupling unit covers a releasable coupling process of a pipetting tip to a coupling unit as well as a permanent coupling of the pipetting tip to the coupling unit. Regarding the latter case, a pipetting needle may be permanently coupled such as screwed to the coupling unit except for an exchange caused by damage or for maintenance purposes.

The term "coupling unit" relates to a unit on a pipetting device which is adapted to interact with and couple to a pipette tip. Such coupling units are well known in the art, e.g. from EP1171240. Also known in the art are pipetting device with more than one coupling units, such as the duplex pipette of EP189900 or multipipetting devices such as the one described in U.S. Pat. No. 7,947,234B2. In all of these devices, the coupling units which interact with and couple to the pipette tip are arranged in parallel relative to each other.

The tilt mechanism may be tiltable around a first pivot. Thus, tilt mechanism is also moved in a tilted position by means of a single pivotal movement around a single pivotal or rotational axis which represents a rather simple construction.

The pipetting device may further comprise a tilt mechanism trigger that is adapted to trigger the tilt mechanism. Thus, the tilting of the first coupling unit must first be initiated or triggered before the first coupling unit is tilted.

The tilt mechanism trigger may be adapted to releasably fix the tilt mechanism in the untilted position. Thus, an unwanted tilting of the first coupling unit is prevented.

The tilt mechanism may comprise a first recess and the tilt mechanism trigger may comprise a pin, wherein the tilt mechanism is fixable in the untilted position by means of an engagement of the pin with the first recess. Thus, an unwanted tilting of the first coupling unit is prevented by means of the engagement of the pin with the first recess.

The tilt mechanism trigger may comprise a trigger lever adapted to pivot around a second pivot. Thus, the tilting movement of the tilt mechanism and the first coupling unit may be initiated or triggered by means of a simple rotational or pivotal movement of the trigger lever.

The pin may be connected to the trigger lever. Thus, the pin may be moved by means of a movement of the trigger lever.

The tilt mechanism may be releasable from the untilted position by means of a disengagement of the pin from the first recess. Thus, while the tilt mechanism may be safely fixed in the untilted position of the first coupling unit, it may be released therefrom by means of a simple movement of the pin out of the first recess.

The pin may be selectively engageable with and disengageable from the first recess by means of pivoting the trigger lever around the second pivot. Thus, while the tilt mechanism may be safely fixed in the untilted position of the first coupling unit, it may be released therefrom by means of a simple pivotal movement of the trigger lever which causes the pin to move out of the first recess.

The tilt mechanism may be releasably fixable in the tilted position, Thus, an unwanted movement back into the untilted position of the first coupling unit and a collision with a vessel by the first coupling unit may be prevented.

The coupling mechanism may further comprise a first coupling lever connected to the first coupling unit, a second coupling lever connected to the second coupling unit, and a first coupling unit protrusion disposed on the first coupling unit. The first coupling lever may comprises a first coupling lever recess. The tilt mechanism may be releasably fixable in the tilted position by means of engagement of the first coupling unit protrusion with the first coupling lever recess. Thus, an unwanted movement back into the untilted position of the first coupling unit and a collision with a vessel by the first coupling unit may be reliably prevented by means of a rather simple construction.

The tilt mechanism may be releasable from the tilted position by means of disengagement of the first coupling unit protrusion from the first coupling lever recess. Thus, by means of a movement of the first coupling unit protrusion out of the first coupling lever recess, the first coupling unit may be moved back into the untilted position.

The first coupling unit protrusion may be selectively engageable with and disengageable from the first coupling lever recess by means of pivoting the tilt mechanism around the first pivot. Thus, by means of a rotational or pivotal movement of the first coupling unit protrusion into or out of the first coupling lever recess, the first coupling unit may be moved into the tilted position or the untilted position.

The tilt mechanism trigger may be adapted to be activated by means of engagement with an activation device of the apparatus for processing a sample. Thus, the tilt mechanism trigger may be activated by means of a device external to or separate from the pipetting device. This avoids the necessity to provide the pipetting device with an actuator for activating the tilt mechanism trigger.

The tilt mechanism trigger may be adapted to be activated by means of a movement of the pipetting device relative to the activation device in a first direction. Thus, by means of a movement of the pipetting device, which may be easily controlled, the tilt mechanism may be activated.

The tilt mechanism may comprise a second recess engageable with a protrusion of the activation device. The tilt mechanism may be tiltable around the first pivot by means of a movement of the pipetting device relative to the activation device in a second direction with the second recess engaged with the protrusion of the activation device. The second direction may be different from the first direction. Thus, the tilt mechanism may be tilted by means of a device external to or separate from the pipetting device. This avoids the necessity to provide the pipetting device itself with an actuator for tilting the tilt mechanism and the first coupling unit.

The second direction may be perpendicular to the first direction. Thus, by means of a movement of the pipetting device, the tilt mechanism may not only be triggered but also be tilted.

The tilt mechanism is tiltable around the first pivot by means of an actuator. Thus, an alternative is realized which may be realized if it is desired to omit the actuation device.

The pipetting device may further comprise a sensor for detection whether the first coupling unit is in the untilted position or the tilted position. The sensor may be a Hall sensor. The pipetting device may further comprise a magnet arranged at the tilt mechanism. Thus, it may be detected whether the first coupling unit is in the untilted position or the tilted position. This ensures that the second pipetting device is immersed in a vessel only if a collision of the first coupling unit and the vessel may not occur.

According to the present invention, an apparatus for processing a sample is disclosed. The apparatus comprises a pipetting device as described before, an input for a first vessel, wherein the vessel comprises a sample or a reagent, a holder for holding a second vessel to which the sample or reagent is transferrable by means of the pipetting device.

The apparatus may further comprise an activation device adapted to activate the tilt mechanism of the pipetting device is disclosed. The pipetting device may comprise a tilt mechanism trigger adapted to releasably fix the tilt mechanism in the untilted position, wherein the tilt mechanism trigger is adapted to be activated by means of engagement with the activation device. The tilt mechanism trigger may be adapted to be activated by means of a movement of the pipetting device relative to the activation device in a first direction. The tilt mechanism may comprise a second recess engageable with a protrusion of the activation device, wherein the tilt mechanism is tiltable around a first pivot by means of a movement of the pipetting device relative to the activation device in a second direction with the second recess engaged with the protrusion of the activation device. The second direction may be different from the first direction. The second direction may be perpendicular to the first direction. The activation device may be arranged at the first vessel or the activation device may be arranged spaced apart from the first vessel.

According to the present invention, a method for pipetting a sample or reagent using a pipetting device as described before is disclosed. The method comprises (a) coupling a second pipetting tip to the second coupling unit, (b) moving the first coupling unit from the untilted position, in which the first coupling unit and the second coupling unit are arranged parallel to one another, into the tilted position, in which the first coupling unit is tilted relative to the second coupling unit, and (c) aspirating a sample or reagent from a first vessel by means of the second pipetting tip while the first coupling unit is in the tilted position.

The first coupling unit may be moved into the tilted position if a ratio of a length of the second pipetting tip and a target immersion depth of the second pipetting tip into the first vessel is below a predetermined threshold. The tilt mechanism of the pipetting device may be activated by means of an activation device. The sample or reagent may be transferred to a second vessel by means of the pipetting device.

FIG. 1 shows a left side perspective view of a pipetting device 100 according to the present disclosure. The pipetting device 100 may be designed as a so-called pipettor. The pipetting device 100 comprises a coupling mechanism 102. The coupling mechanism comprises at least a first coupling unit 104 and a second coupling unit 106. The first coupling unit 104 is adapted to be coupled to a first pipetting tip 108. The second coupling unit 106 is adapted to be coupled to a second pipetting tip 110. The pipetting device 100 further comprises a tilt mechanism 112. The tilt mechanism is adapted to move the first coupling unit 104 between an untilted position, in which the first coupling unit 104 and the second coupling unit 106 are arranged parallel to one another, and a tilted position, in which the first coupling unit 104 is tilted relative to the second coupling unit 106.

Figure 2:
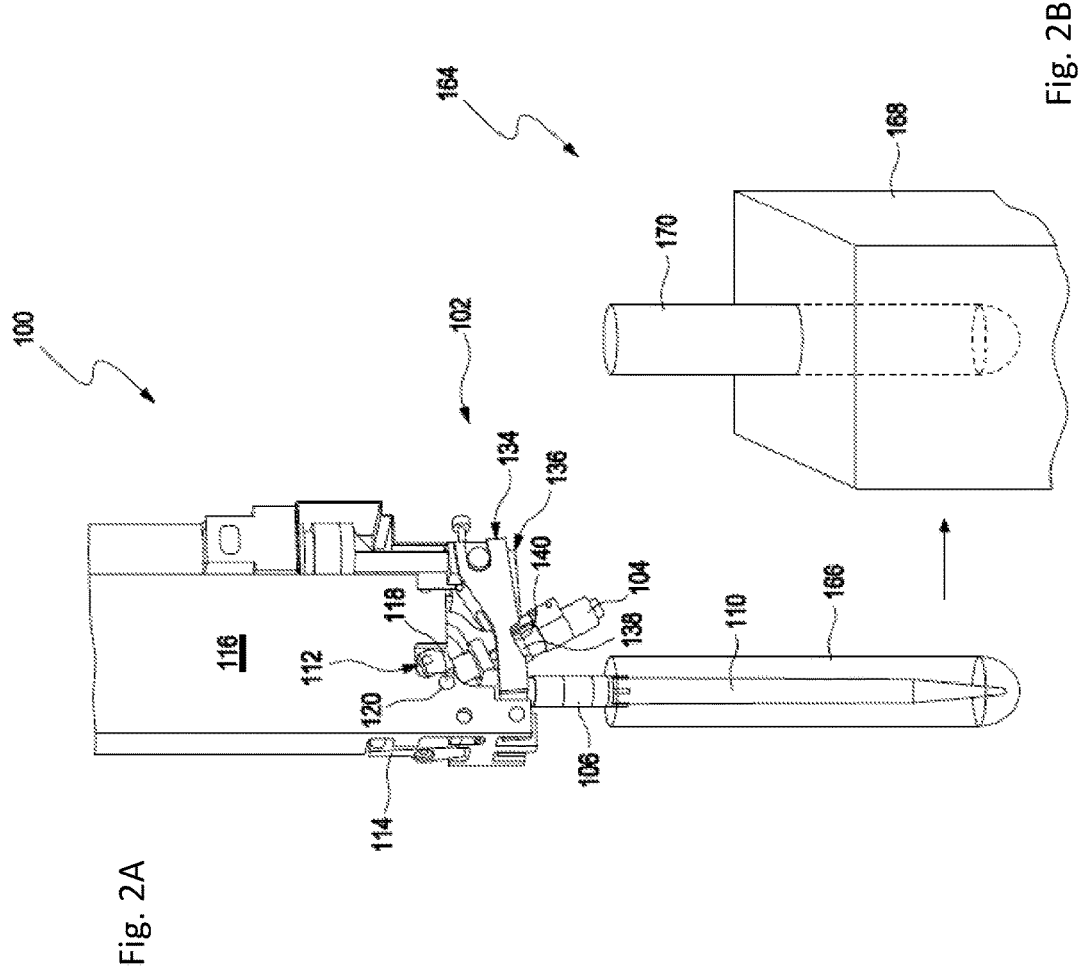
FIGS. 2A and 2B show another left side perspective view of the pipetting device.

FIG. 2 shows another left side perspective view of the pipetting device 100. While FIG. 1 shows the first coupling unit 104 in the untilted position, FIG. 2 shows the first coupling unit 104 in the tilted position, in which the first coupling unit 104 is tilted relative to the second coupling unit 106. The pipetting device further comprises a tilt mechanism trigger 114 adapted to trigger the tilt mechanism 112. The pipetting device 100 further comprises a frame 116. The coupling mechanism 102, the tilt mechanism 112 and the tilt mechanism trigger 114 are at least partially arranged within and supported by the frame 116. As described in more detail below, the tilt mechanism can be activated manually or with the aid of an activation device that is configured to mate with and engage the tilt mechanism trigger, thereby moving the tilt mechanism, resulting in the movement of the coupling unit from an untilted to a tilted position and vice versa.

Particularly, the tilt mechanism 112 is tiltable around a first pivot 118. The first pivot 118 is supported in a correspondingly formed opening 120 located in the frame 116. The opening 120 is located at a side wall of the frame. Thus, the tilt mechanism 112 is tiltable together with the first coupling unit 104. In other words, the tilt mechanism 112 is also moveable between an untilted position and a tilted position. The tilt mechanism and the first coupling unit are connected by a metal tube/cylinder (not shown). In order to prevent collisions of the first pipetting tip 108 or the second pipetting tip 110 with a vessel, it is preferred that the first coupling unit 104 may be tilted or untilted and it may also be locked in either position. Hereinafter, it will be specified in more detail how the locking of the first coupling unit 104 in each of the untilted position and the tilted position is realized.

Figure 3:
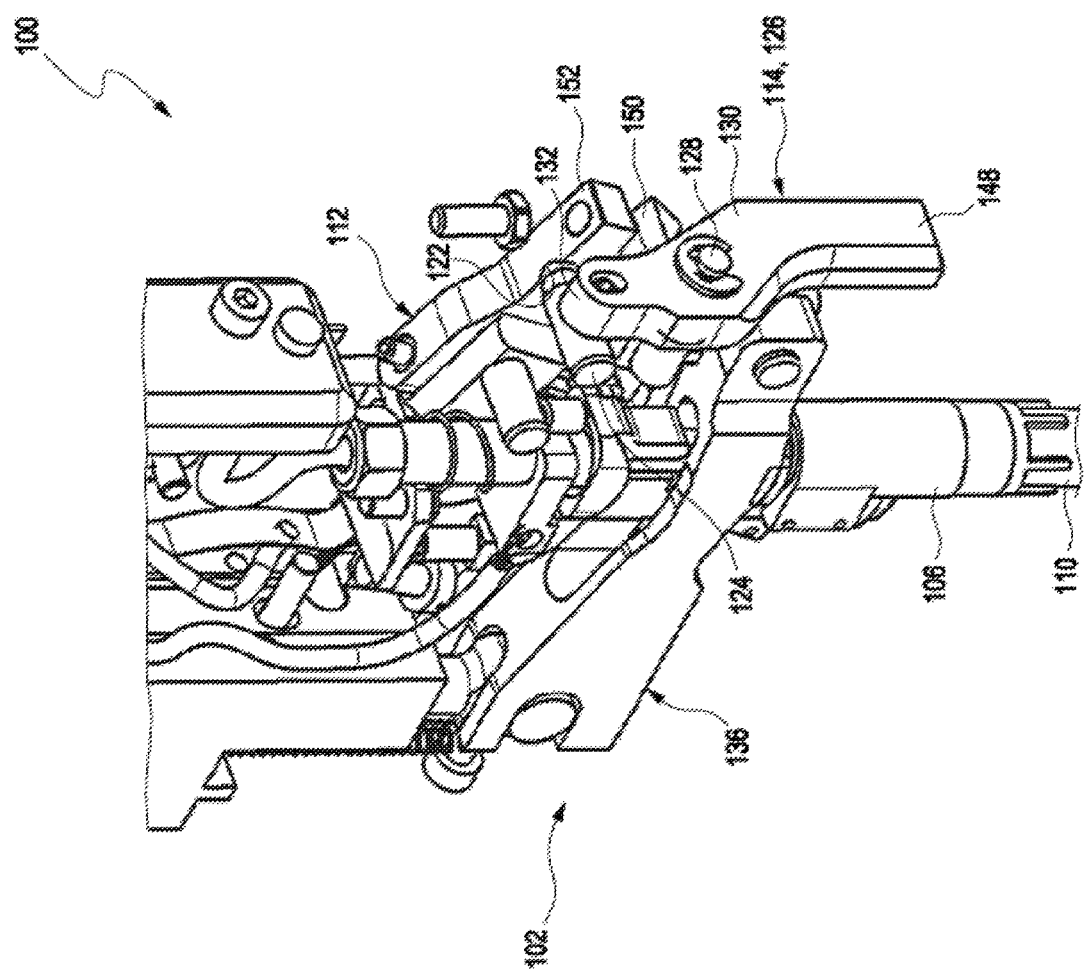
FIG. 3 shows a right side and front perspective view of the pipetting device.

FIG. 3 shows a right side, front perspective view of the pipetting device 100. (It is to be noted that the frame 116 is omitted in FIG. 3 in order to facilitate a better understanding of the present invention.) The tilt mechanism trigger 114 is adapted to move the tilt mechanism 112 from the untilted position to the tilted position. Particularly, the tilt mechanism 112 comprises a first recess 122. The tilt mechanism trigger 114 comprises a pin 124. When the pin 124 is engaged with the first recess 122, the tilt mechanism 112 is fixed in the untilted position and as a result, the associated coupling unit is fixed in the untilted position. On the other hand, when the pin 124 is not engaged with the first recess 122, the tilt mechanism 112 is fixed in the tilted position and as a result, the associated coupling unit is fixed in the tilted position.

In a specific embodiment, the tilt mechanism trigger 114 comprises a trigger lever 126 which pivots around a second pivot 128. The second pivot 128 may be supported by the frame 116. The second pivot 128 is arranged perpendicular with respect to the first pivot 118. The second pivot 128 is fixedly mounted but not functionally coupled to the first pivot 118. In one embodiment, the second pivot 128 is located at a front wall of the frame 116, and it is disposed in the middle portion 130 of the trigger lever 126. The pin 124 is connected to the trigger lever 126, e.g., at the upper end 132 of the trigger lever 126. FIG. 3 shows the pin 124 engaged with the first recess 122. If the trigger lever 126 is pivoted around the second pivot 128 in a counterclockwise direction with respect to the illustration of FIG. 3, the upper end 132 moves to the left with respect to the illustration of FIG. 3, thereby moving the pin 124 to the left and releasing the pin 124 from the first recess 122. On the other hand, if the trigger lever 126 is pivoted in a clockwise direction around the second pivot 128, the upper end 132 moves to the right such that the pin 124 also moves to the right, engaging the pin 124 with the first recess 122 such that the tilt mechanism 112 is blocked from tilting.

As shown in FIG. 2, the coupling mechanism 102 further comprises a first coupling lever 134 and a second coupling lever 136. The first coupling lever 134 is connected to the first coupling unit 104 and the second coupling lever 136 is connected to the second coupling unit 106. The function of such coupling levers is well known to the skilled person, see e.g., U.S. Pat. No. 7,033,543, which is incorporated herein by reference. Reference is also made to the CO-RE system implemented in Hamilton Products, including but not limited to, the Hamilton Microlab STAR Line (Hamilton Company, Reno, Nev.). The coupling mechanism 102 further comprises a first coupling unit protrusion 138 disposed on the first coupling unit 104. The first coupling unit protrusion 138 may be formed as a collar. The first coupling lever 134 comprises a first coupling lever recess 140. Upon engagement of the first coupling unit protrusion 138 with the first coupling lever recess 140, the tilt mechanism 112 is releasably fixable in the tilted position. Analogously, by disengaging the first coupling unit protrusion 138 from the first coupling lever recess 140, the tilt mechanism 112 is released from the tilted position.

In particular, by pivoting the tilt mechanism 112 around the first pivot 118, the first coupling unit protrusion 138 is selectively engageable with and disengageable from the first coupling lever recess 140. For example, with respect to the illustration of FIGS. 1 and 2, if the tilt mechanism 112 is pivoted in a counterclockwise direction around the first pivot 118, the first coupling unit 104 is moved from the untilted position to the tilted position. Further, the first coupling unit protrusion 138 is moved into an engagement with the first coupling lever recess as shown in FIG. 2. Analogously, starting from FIG. 2, if the tilt mechanism 112 is pivoted in a clockwise direction around the first pivot 118, the first coupling unit 104 is moved from the tilted position into the untilted position and the first coupling unit protrusion 138 is disengaged from the first coupling lever recess 140.

Figure 4:
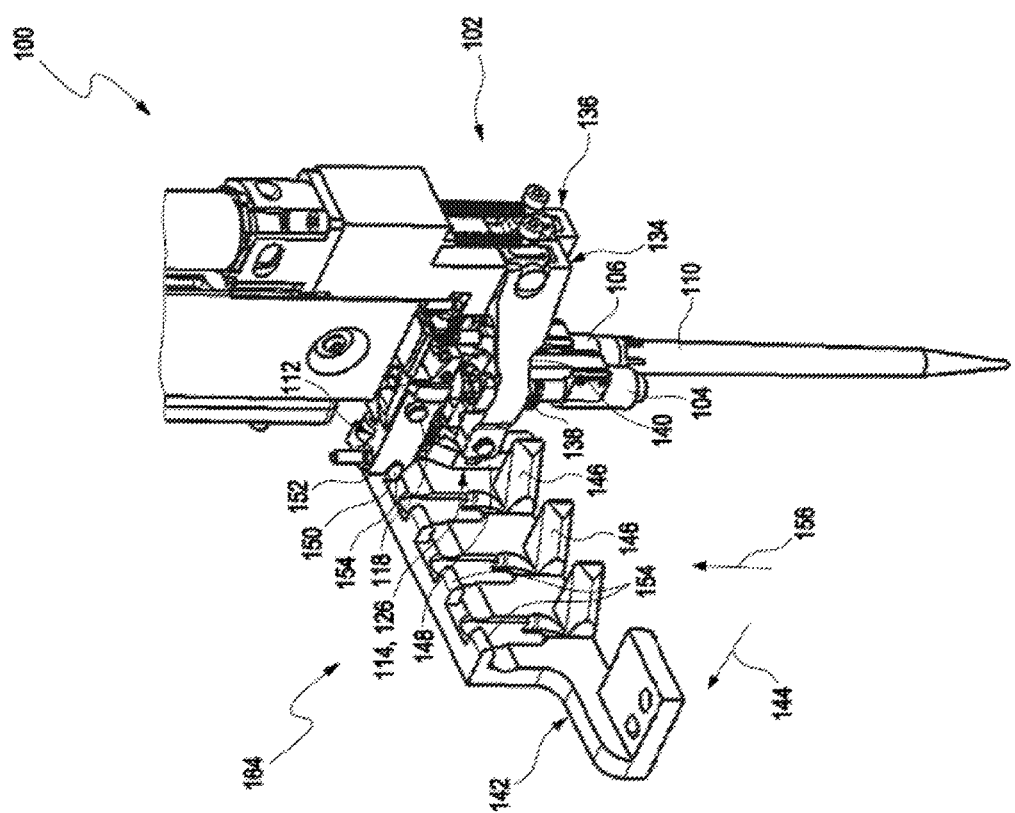
FIG. 4 shows a left side and rear perspective view of the pipetting device.

FIG. 4 shows a left side, rear perspective view of the pipetting device 100. (It is to be noted that the frame 116 is omitted in FIG. 4 in order to facilitate a better understanding of the present invention.) In a specific embodiment, in order to facilitate the movement of the tilt mechanism 112, the present invention provides an activation device 142. More particularly, when the pipetting device 100 moves in a first direction 144, the tilt mechanism trigger 114 is operably engaged with the activation device 142. As shown in FIG. 4, the activation device 142 comprises at least one inclined surface 146. When the pipetting device 100 is moved in the first direction 144 towards the activation device 142, the inclined surface 146 engages a lower end 148 of the trigger lever 126. (It is to be noted that the inclined surface 146 which engages the lower end 148 is hidden by the lower end in the illustration of FIG. 4.) The inclined surface 146 causes the trigger lever 126 to pivot around the second pivot 128 in a clockwise direction with respect to the illustration of FIG. 4, which corresponds to a counterclockwise direction with respect to the illustration of FIG. 3.

Figure 5:
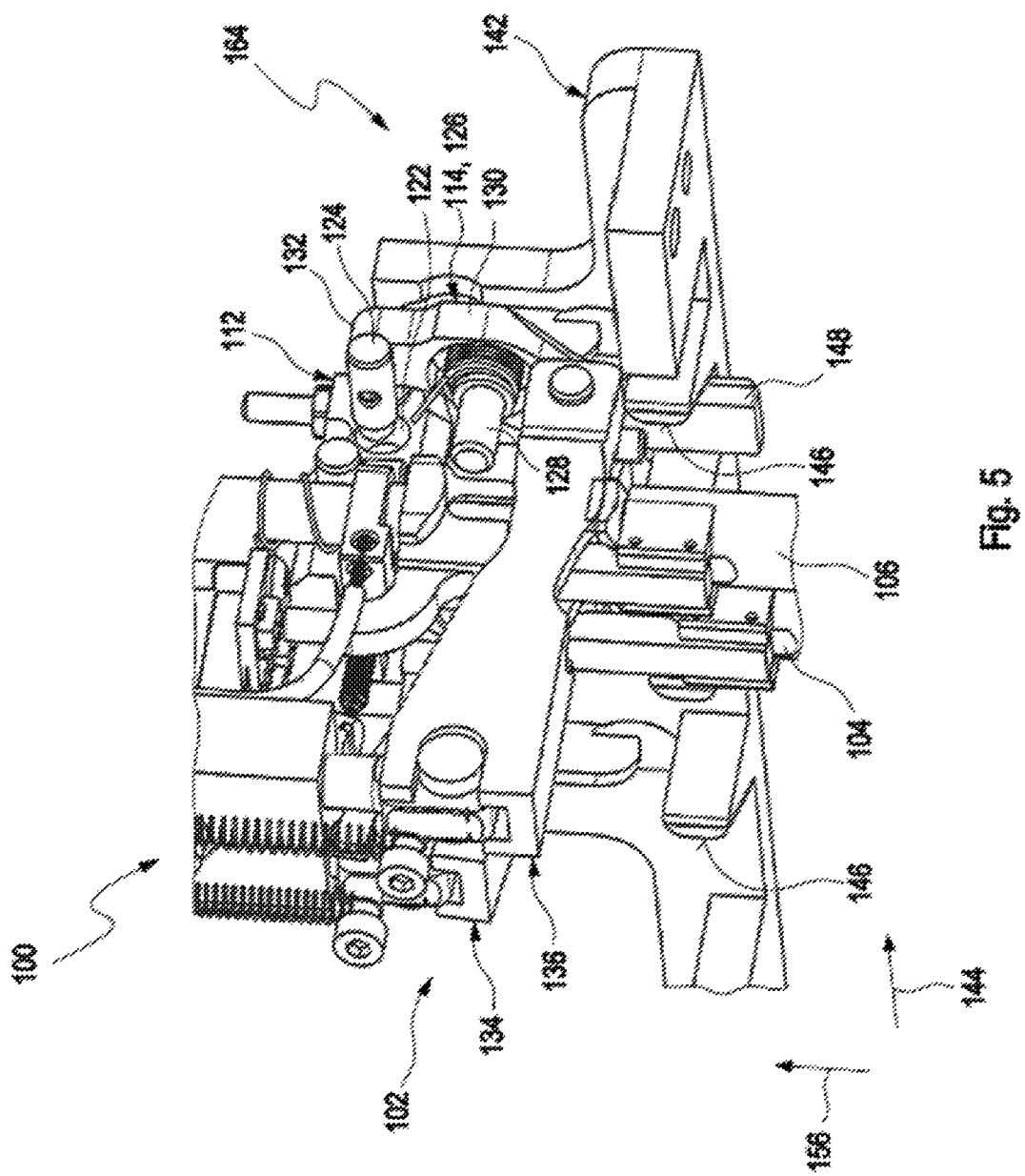
FIG. 5 shows a right side and rear perspective view of the pipetting device.

FIG. 5 shows a right side, rear perspective view of the pipetting device 100. (It is to be noted that the frame 116 is omitted in FIG. 5 in order to facilitate a better understanding of the present invention.) Upon engagement of the inclined surface 146 with the lower end 148 of the trigger lever 126, the pin 124 is released from the first recess 122 in the manner described above. FIG. 5 shows the pin 124 moved out of the first recess 122. Thus, the movement of the pipetting device 100 in the first direction 144 towards the activation device 142 serves to release the fixation of the tilt mechanism 112. In order to tilt the tilt mechanism 112, another process in connection with the activation device 142 is realized.

Figure 6:
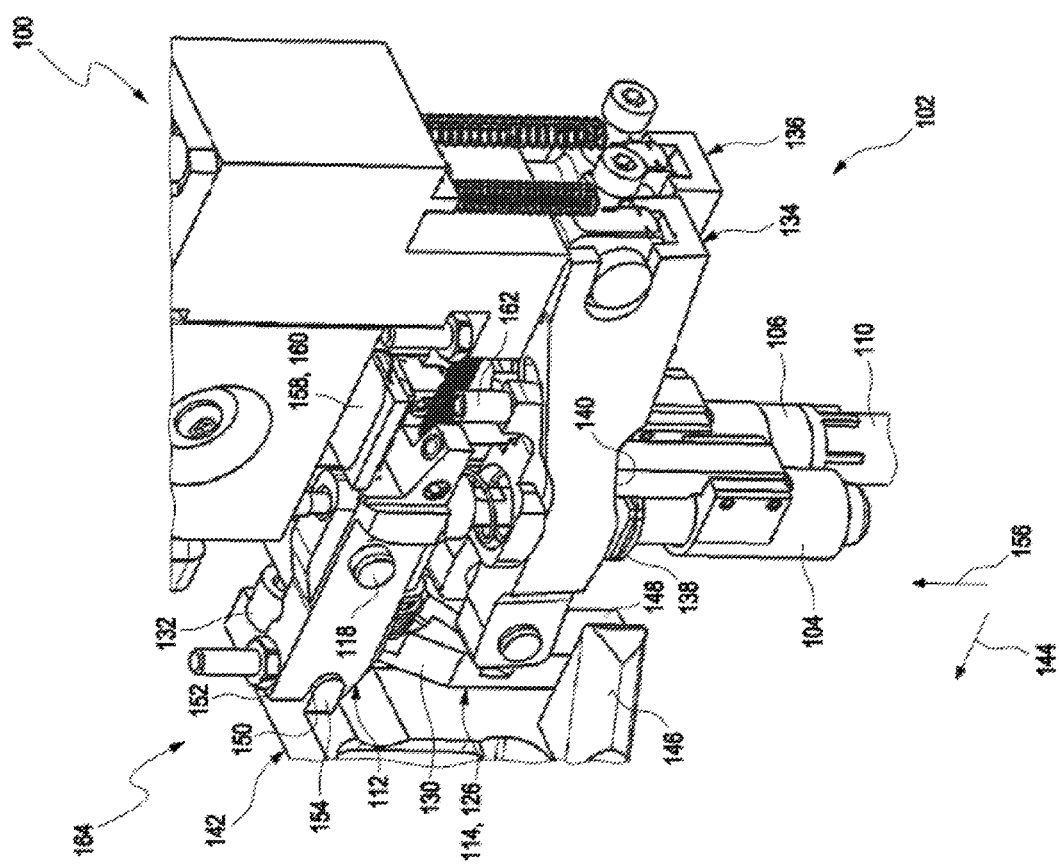
FIG. 6 shows a left side and rear perspective view of the pipetting device.

FIG. 6 shows a left side, rear perspective view of the pipetting device 100. (It is to be noted that the frame 116 is omitted in FIG. 6 in order to facilitate a better understanding of the present invention.) Particularly, the tilt mechanism 112 comprises a second recess 150 arranged at a front end 152 of the tilt mechanism 112. The front end 152 faces the activation device 142. The activation device 142 comprises a protrusion 154. The protrusion 154 is arranged above the inclined surface 146. The second recess 150 is engageable with the protrusion 154. By means of a movement of the pipetting device 100 relative to the activation device 142 in a second direction 156 with the second recess 150 engaged with the protrusion 154, the tilt mechanism 112 is tiltable around the first pivot 118 in the manner described above. The second direction 156 is different from the first direction 144. More particularly, the second direction 156 is perpendicular to the first direction 144.

If the pipetting device 100 is moved in the second direction 156 corresponding to an upward movement with respect to the illustration of FIG. 6, the front end 152 is moved downwards with the second recess 150 engaged with the protrusion 154 such that the tilt mechanism 112 pivots in counterclockwise direction around the first pivot 118. This construction allows for omitting an additional actuator for realizing the tilt movement of the tilt mechanism 112. Needless to say, according to an alternative embodiment of the present invention (not shown in detail), the tilt mechanism 112 may be tiltable around the first pivot 118 by means of an actuator. Further, as shown in FIG. 6, the pipetting device 100 may comprise a sensor 158 for detection whether the first coupling unit 104 is in the untilted position or the tilted position. The sensor 158 may be a Hall sensor 160. For this purpose, a magnet 162 may be arranged at the tilt mechanism 112. If the magnet 162 faces the Hall sensor 160, the Hall sensor 160 will output a signal indicating that the first coupling unit 104 is in the untilted position. If the magnet 162 does not face the Hall sensor 160 because the magnet 162 has been moved away from the Hall sensor 160, the Hall sensor 160 will not output a signal indicating that the first coupling unit 104 is in the tilted position.

FIG. 7 shows a schematic illustration of an apparatus 164 for processing a sample or reagent. The pipetting device 100 may be part of the apparatus 164. The apparatus 164 further comprises an input 171 for a first vessel 166, which comprises a sample or reagent, and as shown in FIG. 2(b), a holder 168 for holding a second vessel 170 to which the sample or reagent is transferrable by means of the pipetting device 100. The first vessel 166 and/or the second vessel 170 may be formed as a tube. The apparatus 164 for processing a sample further comprises the activation device 142. The activation device 142 may be arranged at the first vessel 166. Alternatively, the activation device 142 may be arranged spaced apart from the first vessel 166. The tilting of the first coupling unit 104 may alternatively be triggered and carried out by a vessel comprising a sample to be pipetted.

With the pipetting device according to the present invention, the sample or reagent may be pipetted. Particularly, the first pipetting tip 108 may optionally be coupled to the first coupling unit 104 or not whereas the second pipetting tip 110 is coupled to the second coupling unit 106. Such a coupling process is well known to the skilled person such that a description of the coupling process is omitted. Then, the first coupling unit 104 is moved from the untilted position into the tilted position such that the first coupling unit 104 is tilted relative to the second coupling unit 106. Then, a sample or reagent from the first vessel 166 is aspirated by means of the second pipetting tip 110. Particularly, the first coupling unit 104 is moved into the tilted position if a ratio of a length of the second pipetting tip 110 and a target immersion depth of the second pipetting tip 110 into the first vessel 166 is below a predetermined threshold. With other words, if the second pipetting tip 110 is not long enough in order to comply with a target immersion depth, then the first coupling unit 104 is moved into the tilted position in order to avoid a collision of the first coupling 104 unit with the first vessel 166 into which the second pipetting tip 110 is immersed. In case the first coupling unit 104 has to be moved into the tilted position, the first pipetting tip 108 is not coupled to the first coupling unit 104. Finally, the pipetting device 100 is moved to the second vessel 170 and the sample or reagent is dispensed from the second pipetting tip 110 into the second vessel 170. Thus, the sample or reagent is transferred from the first vessel 166 to the second vessel 170 by means of the pipetting device 100.

It is explicitly stated that the coupling mechanism 102 may comprise more than the first coupling unit 104 and the second coupling unit 106. In other words, the coupling mechanism 102 may comprise more than two coupling units in order to allow to couple more than two pipetting tips to the coupling units. For example, the coupling mechanism 102 may comprise 4, 6, 8, 10 or even more coupling units in order to allow for coupling of 4, 6, 8, 10 or even more pipetting tips. In this case, the tilt mechanism 112 may be designed in the above manner so as to allow to tilt every second coupling unit in a row.

FIGS. 8 (a) to 8(l) show the movement of tilt mechanism 112, trigger lever 126 and first coupling unit 104 upon activation with the activation device 142.

FIG. 8(a) shows the trigger lever 126 position when the coupling unit 104 is in the untilted position and pin 124 is in the locked position. When the pin 124 is in the locked position, the tilt mechanism 112 cannot be moved. FIG. 8(b) corresponds to FIG. 8(a), except that the activation device was removed from the drawing to better show the mechanism. FIG. 8(c) shows a close-up from the left side of the pipetting device shown in FIGS. 8(a) and 8(b) with the trigger lever 126, first coupling unit 104 and tilt mechanism 112 in the unactivated position and pin 124 in the locked position.

FIG. 8(d) shows the activation of the trigger lever 126 by the activation device 142. The lower part of the activation device 142 moves the lower part of the trigger lever 126, thereby moving the trigger 126 lever counter-clockwise, and thus, moving pin 124 into the unlocked position. FIG. 8(e) corresponds to FIG. 8(d), except that the activation device was removed from the drawing to better show the mechanism. FIG. 8(f) shows a close-up from the left side of the pipetting device shown in FIGS. 8(d) and 8(e) with the trigger lever 126 moved counter-clockwise, first coupling unit 104 still in the untilted position, pin 124 in the unlocked position and tilt mechanism 112 in the unactivated position.

FIG. 8(g) shows the device after movement of the tilt mechanism 112 and first coupling unit 104 when the activation device 142 is moved downwards relative to the trigger lever 126. The tilt mechanism 112 is moved downwards, thereby tilting the first coupling unit 104. The trigger lever 126 remains stationary in this step. FIG. 8(h) corresponds to FIG. 8(g), except that the activation device was removed from the drawing to better show the mechanism. FIG. 8(i) shows a close-up from the left side of the pipetting device shown in FIGS. 8(g) and 8(h), where the tilt mechanism 112 is in a lower position compared to the previous states, and first coupling unit 104 is partly tilted.

Figures 8J, 8K, 8L:
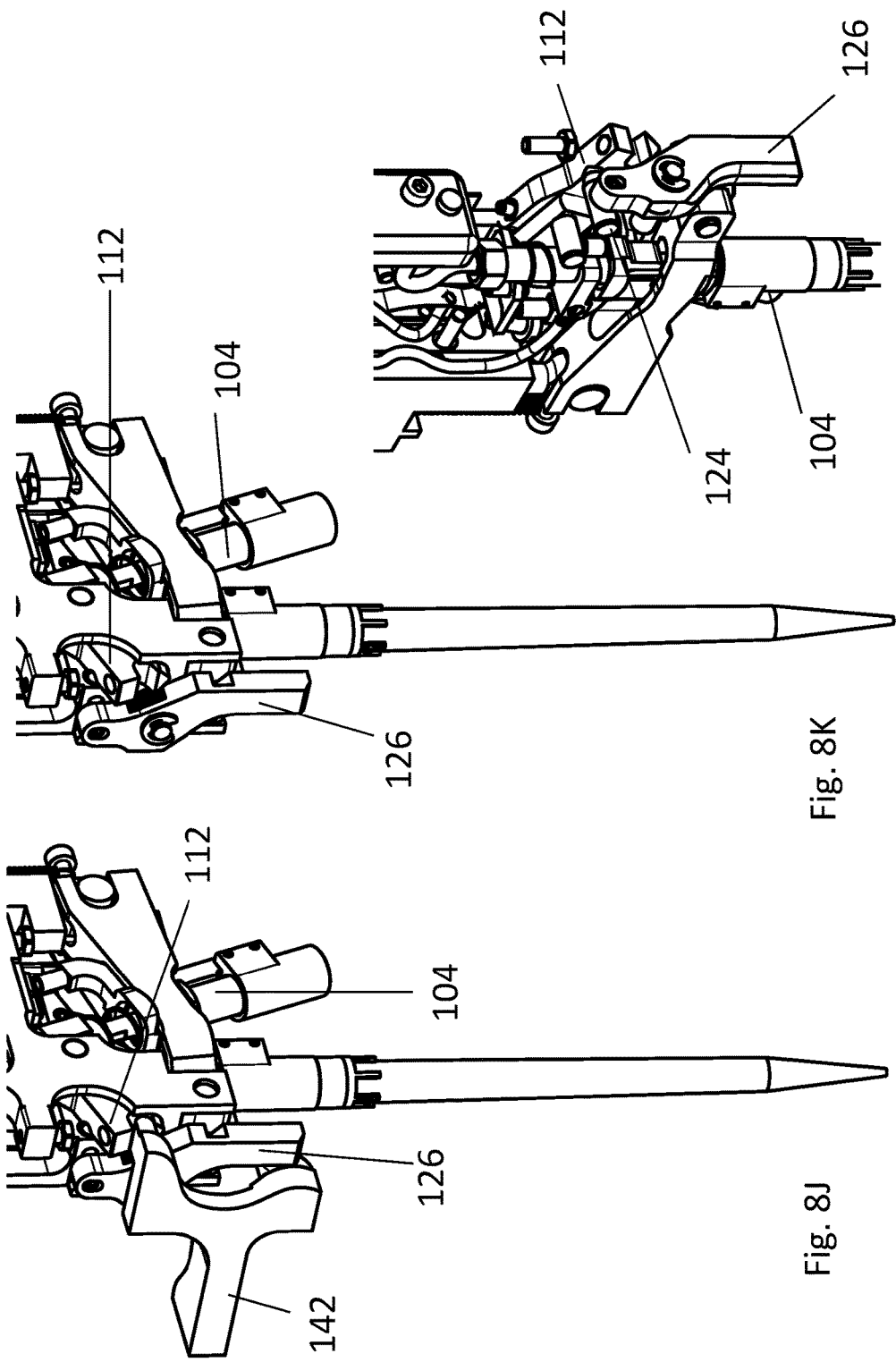
FIGS. 8A-8O show a detailed view of the tilt mechanism and the progression of the elements of the tilt mechanism from the untilted to the tilted position.

FIG. 8(j) shows the device after movement of the first coupling unit 104 into the final tilt position. Activation device 142 is moved even further downwards compared to FIG. 8(g). By this, the tilt mechanism 112 is also moved further downwards compared to FIG. 8(g), and the first coupling unit 104 is tilted more than in FIG. 8(g). The trigger lever 126 remains stationary in this step, so does pin 124, which remains in the unlocked position. FIG. 8(k)

corresponds to FIG. 8(j), except that the activation device was removed from the drawing to better show the mechanism. FIG. 8(l) shows a close-up from the left side of the pipetting device shown in FIGS. 8(k) and 8(j), where the tilt mechanism 112 is in a lower position compared to FIG. 8(i), and first coupling unit 104 is fully tilted.

FIG. 8(m) shows the tilted pipetting device after removal of the activation device 142. The trigger lever 126 moves slightly clockwise, and, thereby, pin 124 is moved into the locked position. This leads to a locking of the tilt mechanism 112 in the lowest position and a locking of the first coupling unit 104 in the tilted position. FIG. 8(n) corresponds to FIG. 8(m), except that the activation device was removed from the drawing to better show the mechanism. FIG. 8(o) shows a close-up from the left side of the pipetting device shown in FIGS. 8(m) and 8(n), where the trigger level 126 is slightly moved clockwise, compared to FIG. 8(i), the tilt mechanism 112 is in its lowest position and first coupling unit 104 is fully tilted and pin 124 is seen, which is now in the locked position, thereby locking the fully tilted first coupling unit 104 in its tilted position.

The present application is not to be limited in scope by the specific embodiments described herein. Indeed, various modifications in addition to those described herein will become apparent to those skilled in the art from the foregoing description and accompanying figures. Such modifications are intended to fall within the scope of the claims. Various publications are cited herein, the disclosures of which are incorporated by reference in their entireties.

The invention claimed is:

1. A pipetting device for an apparatus for processing a sample or reagent, comprising a frame including the following elements arranged within and supported by the frame:
   a coupling mechanism including at least a first coupling unit adapted to be coupled to a first pipetting tip and a second coupling unit adapted to be coupled to a second pipetting tip,
   a tilt mechanism configured to move the first coupling unit between an untilted position, in which the first coupling unit and the second coupling unit are arranged parallel to one another, and a tilted position, in which the first coupling unit is tilted relative to the second coupling unit, and
   a tilt mechanism trigger adapted to trigger the tilt mechanism by engagement with an activation device,
   wherein movement of the pipetting device relative to the activation device engages with and activates the tilt mechanism, fixing the tilt mechanism in the untilted position, and thereby fixing the first coupling unit in the untilted position.

2. The pipetting device of claim 1, wherein the tilt mechanism is tiltable around a first pivot.

3. The pipetting device of claim 2, wherein the tilt mechanism comprises a recess and the tilt mechanism trigger comprises a pin and upon engagement of the tilt mechanism trigger, the pin engages with the recess, thereby fixing the tilt mechanism in the untilted position.

4. The pipetting device of claim 1, wherein the tilt mechanism is releasably fixed in the untilted position.

5. The pipetting device of claim 1, wherein the tilt mechanism is releasably fixed in the tilted position.

6. The pipetting device of claim 2, wherein the tilt mechanism comprises a second recess engageable with a protrusion of the activation device, wherein the tilt mechanism is tiltable around the first pivot by means of a movement of the pipetting device relative to the activation device.

7. The pipetting device of claim 1, further comprising a sensor for detecting whether the first coupling unit is in the untilted position or the tilted position.

8. An apparatus for processing a sample or reagent, comprising a pipetting device of claim 1, an input for a first vessel, said first vessel comprising a sample or reagent, and a holder for holding a second vessel to which the sample or reagent is transferrable by the pipetting device.

9. An apparatus for processing a sample or reagent of claim 8, further comprising an activation device adapted to activate the tilt mechanism of the pipetting device.

10. A method for pipetting a sample or reagent using a pipetting device according to claim 1, comprising:
   (a) coupling a second pipetting tip to the second coupling unit,
   (b) moving the first coupling unit from the untilted position, in which the first coupling unit and the second coupling unit are arranged parallel to one another, into the tilted position, in which the first coupling unit is tilted relative to the second coupling unit, and
   (c) aspirating the sample or reagent from a first vessel by means of the second pipetting tip while the first coupling unit is in the tilted position.

11. A method of claim 10, wherein the first coupling unit is moved into the tilted position if a ratio of a length of the second pipetting tip and a target immersion depth of the second pipetting tip into the first vessel is below a predetermined threshold.

12. A method of claim 10, wherein the tilt mechanism of the pipetting device is activated upon engagement with an activation device.

13. A method of claim 10, further comprising transferring the sample or reagent to a second vessel using the pipetting device.

* * * * *

UNITED STATES PATENT AND TRADEMARK OFFICE
CERTIFICATE OF CORRECTION

PATENT NO. : 10,300,480 B2  
APPLICATION NO. : 15/291960  
DATED : May 28, 2019  
INVENTOR(S) : Hans-Rudolf Bachmann and Rolf Schneebeli Page 1 of 1

It is certified that error appears in the above-identified patent and that said Letters Patent is hereby corrected as shown below:

On the Title Page

Item (30) should read:  
Foreign Application Priority Data  
October 13, 2015 (EP) 15189533.1

Signed and Sealed this  
Ninth Day of July, 2019

Andrei Iancu  
*Director of the United States Patent and Trademark Office*